United States Patent
Babula et al.

(10) Patent No.: US 7,225,406 B2
(45) Date of Patent: *May 29, 2007

(54) PROBLEM-SOLUTION RESOURCE SYSTEM FOR MEDICAL DIAGNOSTIC EQUIPMENT

(75) Inventors: Deborah Ann Babula, Franklin, WI (US); David Thomas Mehring, Sussex, WI (US); Ronald V. Larson, Waukesha, WI (US); Thomas L. Lamoureux, Waukesha, WI (US)

(73) Assignee: GE Medical Systems, Inc., Pewaukee, WI (US)

( * ) Notice: Subject to any disclaimer, the term of this patent is extended or adjusted under 35 U.S.C. 154(b) by 508 days.

This patent is subject to a terminal disclaimer.

(21) Appl. No.: 10/287,359

(22) Filed: Nov. 4, 2002

(65) Prior Publication Data

US 2003/0061071 A1 Mar. 27, 2003

Related U.S. Application Data

(63) Continuation of application No. 09/449,298, filed on Nov. 24, 1999, now Pat. No. 6,509,914.

(51) Int. Cl.
*G06F 15/00* (2006.01)
*G06F 13/00* (2006.01)

(52) U.S. Cl. .................. 715/736; 715/737; 715/744

(58) Field of Classification Search ............. 715/736, 715/737, 744, 749, 762, 765, 771, 804, 805, 715/840
See application file for complete search history.

(56) References Cited

U.S. PATENT DOCUMENTS

| | | | |
|---|---|---|---|
| 5,452,416 A * | 9/1995 | Hilton et al. | 715/783 |
| 5,603,323 A | 2/1997 | Pflugrath et al. | |
| 5,655,084 A | 8/1997 | Pinsky et al. | |
| 5,675,744 A | 10/1997 | Tsujii | |
| 5,715,823 A | 2/1998 | Wood et al. | |
| 5,790,793 A | 8/1998 | Higley | |
| 5,995,101 A | 11/1999 | Clark et al. | |
| 6,078,935 A * | 6/2000 | Nielsen | 715/513 |

* cited by examiner

*Primary Examiner*—Cao (Kevin) Nguyen
(74) *Attorney, Agent, or Firm*—Fletcher Yoder

(57) ABSTRACT

A technique is disclosed for providing problem and solution information, such as that relating to a particular application or protocol, to medical diagnostic institutions and systems. The information is created and stored on machine readable media. A user may enter a problem query at a user interface at the diagnostic institution or system and search a database of information located at a centralized service facility. A list of solutions to the query is displayed at the diagnostic institution. The user may then select and display a desired solution from the user interface. The particular solution may include textual and exemplary image descriptions of the solution. Moreover, additional links may be provided to access other related sources of information. The information stored on the machine readable media may be easily updated by adding new case problems and associated solutions as well as new solutions to existing case problems.

32 Claims, 12 Drawing Sheets

PROBLEM-SOLUTION RESOURCE SYSTEM FOR MEDICAL DIAGNOSTIC EQUIPMENT

This application is a Continuation of application Ser. No, 09/449,298, filed Nov. 24, 1999 now U.S. Pat. No. 6,509,914.

FIELD OF THE INVENTION

The present invention relates generally to medical diagnostic and imaging systems which are configured to execute protocols for examinations, image acquisition, and so forth. More particularly, the invention relates to a technique for making problem and solution information readily available to a system user, for easily searching such information, and for transmitting search results to the diagnostic system, such as a scanner console or departmental PC where the user can then implement them.

BACKGROUND OF THE INVENTION

Medical diagnostic and imaging systems are ubiquitous in modem health care facilities. Such systems provide invaluable tools for identifying, diagnosing and treating physical conditions and greatly reduce the need for surgical diagnostic intervention. In many instances, final diagnosis and treatment proceed only after an attending physician or radiologist has complemented conventional examinations with detailed images of relevant areas and tissues via one or more imaging modalities.

Currently, a number of modalities exist for medical diagnostic and imaging systems. These include computed tomography (CT) systems, x-ray systems (including both conventional and digital or digitized imaging systems), magnetic resonance (MR) systems, positron emission tomography (PET) systems, ultrasound systems, nuclear medicine systems, and so forth. In many instances, these modalities complement one another and offer the physician a range of techniques for imaging particular types of tissue, organs, physiological systems, and so forth. Health care institutions often dispose of several such imaging systems at a single or multiple facilities, permitting their physicians to draw upon such resources as required by particular patient needs.

Modem medical diagnostic systems typically include circuitry for acquiring image data and for transforming the data into a useable form which is then processed to create a reconstructed image of features of interest within the patient. The image data acquisition and processing circuitry is often referred to as a "scanner" regardless of the modality, because some sort of physical or electronic scanning often occurs in the imaging process. The particular components of the system and related circuitry, of course, differ greatly between modalities due to their different physics and data processing requirements.

In medical diagnostic systems of the type described above, imaging or examination protocols are commonly employed for performing a series of functions, typically designed to produce image data which can be later reconstructed. While the particular physics of the system dictates the types of protocols which are employed, all modalities will execute a range of such protocols to provide specific types of images as required by the specific anatomy or diagnosis involved. For example, in MRI systems pulse sequences are typically defined by protocols that include a series of pulses designed to excite gyromagnetic material in a subject of interest and to sense emissions from the gyromagnetic material in response to the pulses. In CT systems, other protocols are used to command x-ray emissions and movements of a system gantry as well as other components for successive acquisition of a multitude of image data sets which are later reconstructed into a useful image.

From time to time, scanner operators may have questions or problems, or may simply desire specific information as to the operation of the scanner. Such information may pertain to configuration specifications, execution of particular protocols, as well as tips on more productive use of the equipment, to name a few. Options available to scanner operators include referencing textual manuals and contacting scanner service centers to obtain answers. While these approaches are generally satisfactory, they are not without drawbacks. For example, textual manuals may not be readily accessible at the scanner location, but rather stored in a different room or building. Textual manuals also may not contain the most up-to-date information. Updating these manuals entails republishing and distributing them, which can be costly and time-consuming. Alternatively, scanner operators can contact service centers via telephone or email with their questions. The calls or emails are typically placed in a queue and addressed in turn. One disadvantage with contacting a service center can be the lengthy response time. Often scanner operators with simple or frequently asked questions must wait in a long queue before their questions are answered.

There is a need, therefore, for an improved system for answering questions about protocols and medical diagnostic systems. There is a particular need for a technique which is user friendly to the scanner operator and provides a clear listing of available solutions as well as new solutions as they become available. There is also a need for an improved technique for updating the information available to the scanner operator.

SUMMARY OF THE INVENTION

The invention provides a novel approach to handling problem and solution information designed to respond to these needs. The system may be integrated in a scanner interface which includes pages accessible through a browser-type or other graphical user interface system. At least one of the pages may be reserved for entering key words and phrases for a query. Additional pages may be devoted to a listing and description of solutions available for the particular scanner. The technique may also be employed on centralized management stations, such as a station linking several scanners in a radiological department of a medical institution. The interface may also permit additional information to be loaded or requested by simply selecting the additional information from a menu.

In a preferred arrangement, up-to-date problem and solution information may be made available through an interactive communications system which links the scanners to a centralized service facility. The communications system enables the operations personnel to submit a problem query to the service facility and to search the service facility library. The library may be installed on machine readable media, and information from the library may be transmitted via a network. The service facility may transmit a list of available solutions to the operations personnel. The solutions may then be downloaded or transmitted automatically or upon request by the institution. The technique allows information for a large variety of scanners, scanner types, and modalities to be easily distributed through the service center. Distribution of information may also be performed by the system, such as for transmitting protocols or taking other actions or viewing other pages in accordance with subscriptions and so forth.

DETAILED DESCRIPTION OF THE INVENTION

Figure 1:
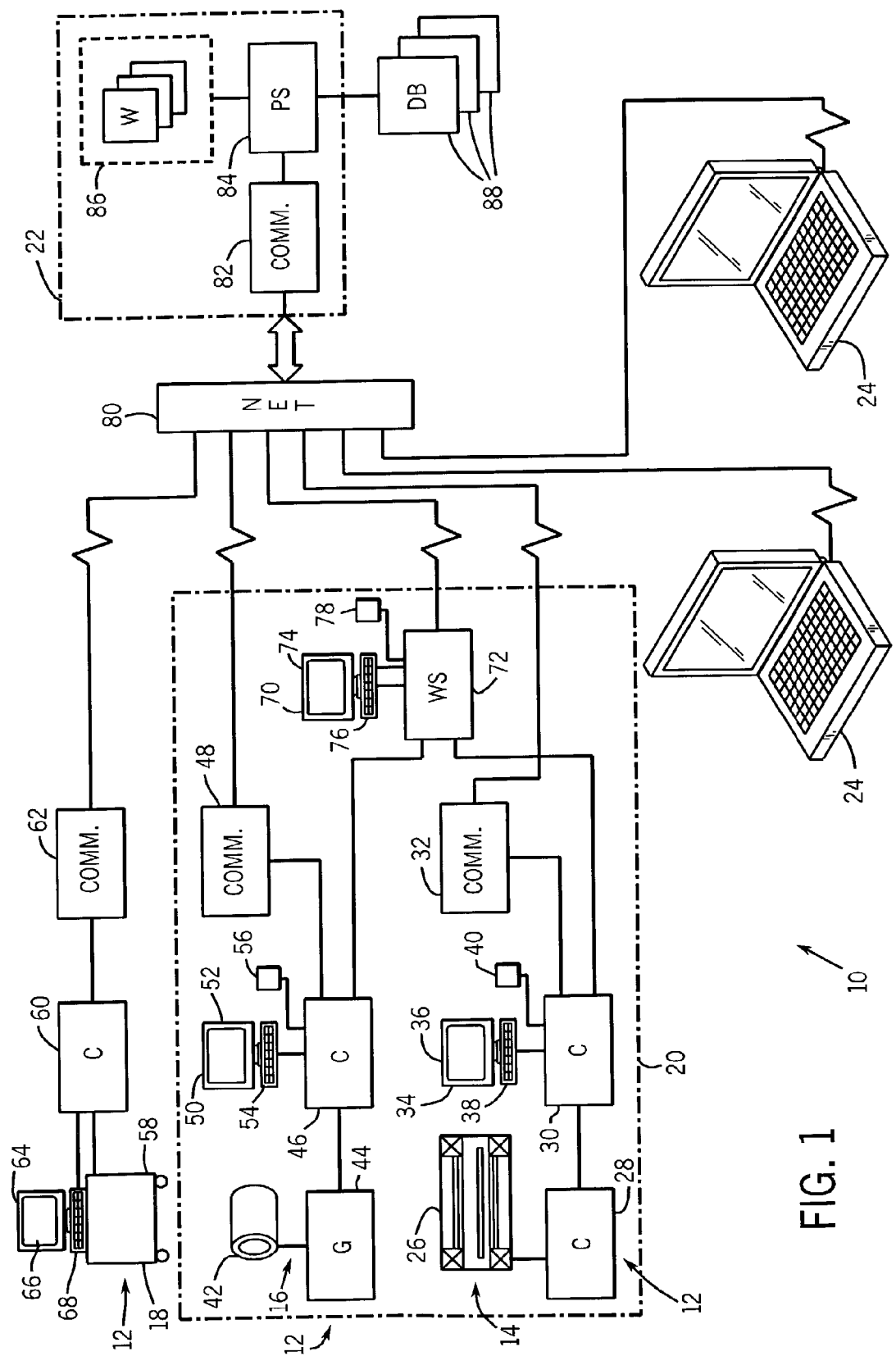
FIG. 1 is a diagrammatical representation of a series of medical diagnostic systems coupled to a service facility via a network connection for providing remote service and data interchange between the diagnostic systems and the service facility.

Turning now to the drawings, and referring first to FIG. 1, a service system 10 is illustrated for providing remote service to a plurality of medical diagnostic systems 12. In the embodiment illustrated in FIG. 1, the medical diagnostic systems include a magnetic resonance imaging (MRI) system 14, a computed tomography (CT) system 16, and an ultrasound imaging system 18. The diagnostic systems may be positioned in a single location or facility, such as a medical facility 20, or may be remote from one another as shown in the case of ultrasound system 18. The diagnostic systems are serviced from a centralized service facility 22. Moreover, a plurality of field service units 24 may be coupled in the service system for transmitting service requests, verifying service status, transmitting service data and so forth as described more fully below.

In the exemplary embodiment of FIG. 1, several different system modalities are provided with remote service by the service facility. These and other modalities may be similarly serviced by the service facility, depending upon the capabilities of the service facility, the types of diagnostic systems subscribing to service contracts with the facility, as well as other factors. In general, however, the present technique is particularly well suited to providing remote service to a wide variety of medical diagnostic system modalities, including MRI systems, CT systems, ultrasound systems, positron emission tomography (PET) systems, nuclear medicine systems, and so forth. Moreover, the various modality systems serviced in accordance with the present techniques may be of different type, manufacture, and model. Service requests and data transmitted between the systems and the service facility include data for identifying the type and modality of the serviced system, as well as data specifically adapted to the system modality and model. It should also be noted that, as used herein, the term "service request" is intended to include a wide range of inquiries, comments, suggestions and other queries or messages generated by a diagnostic system or an institution in which a system is disposed or managed. In particular, such requests may relate to problems occurring on systems, applications questions, questions of a general nature, questions relating to financial or subscription arrangements, information sharing, reports, applications, protocols, and so forth.

Depending upon the modality of the systems, various subcomponents or subsystems will be included. In the case of MRI system 14, such systems will generally include a scanner 26 for generating pulsed magnetic fields and for collecting signals from emissions by gyromagnetic material within a subject of interest. The scanner is coupled to a control and signal detection circuit 28 which, in turn, is coupled to a system controller 30. System controller 30 includes a uniform platform for interactively exchanging service requests, messages and data with service facility 22 as described more fully below. System controller 30 is linked to a communications module 32, which may be included in a single or separate physical package from system controller 30. System controller 30 is also linked to an operator station 34 which will typically include a computer monitor 36, a keyboard 38, as well as other input devices 40, such as a mouse. In a typical system, additional components may be included in system 14, such as a printer or photographic system for producing reconstructed images based upon data collected from scanner 14. Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics. More particularly, equipment benefiting from the present techniques may include imaging systems, clinical diagnostic systems, physiological monitoring systems and so forth.

Similarly, CT system 16 will typically include a scanner 42 which detects portions of x-ray radiation directed through a subject of interest. Scanner 42 is coupled to a generator and controller, as well as to a signal acquisition unit, represented collectively at reference numeral 44, for controlling operation of an x-ray source and gantry within scanner 42, and for receiving signals produced by a detector array moveable within the scanner. The circuitry within the controller and signal acquisition components is coupled to a system controller 46 which, like controller 30 mentioned above, includes circuitry for commanding operation of the scanner and for processing and reconstructing image data based upon the acquired signals. System controller 46 is linked to a communications module 48, generally similar to communications module 32 of MRI system 14, for transmitting and receiving data for remote service of system 16. Also, system controller 46 is coupled to an operator station 50 which includes a computer monitor 52, a keyboard 54, as well as other input devices 56, such as a mouse. Moreover, like MRI system 14, CT system 16 will generally include a printer or similar device for outputting reconstructed images based upon data collected by scanner 42.

Other modality devices will include circuitry and hardware particularly configured for acquiring or producing signals in accordance with their particular design. In particular, in the case of ultrasound system 18, such systems will generally include a scanner and data processing unit 58 for transmitting ultrasound signals into a subject of interest, and for acquiring resultant signals which are processed for reconstructing a useful image. The system includes a system controller 60 which regulates operation of scanner 58 and which processes acquired signals to reconstruct the image. Moreover, system 18 includes a communications module 62 for transmitting service requests, messages and data between system controller 60 and service facility 22. System 18 also includes an operators station 64, including a monitor 66, as well as input devices such as a keyboard 68.

Where more than one medical diagnostic system is provided in a single facility or location, as indicated in the case of MRI and CT systems 14 and 16 in FIG. 1, these may be coupled to a management station 70, such as in a radiology department of a hospital or clinic. The management station may be linked directly to controllers for the various diagnostic systems, such as controllers 30 and 46 in the illustrated embodiment. The management system may include a computer workstation or personal computer 72 coupled to the system controllers in an intranet configuration, in a file sharing configuration, a client/server arrangement, or in any other suitable manner. Moreover, management station 70 will typically include a monitor 74 for viewing system operational parameters, analyzing system utilization, and exchanging service requests and data between the facility 20 and the service facility 22. Input devices, such as a standard computer keyboard 76 and mouse 78, may also be provided to facilitate the user interface. It should be noted that, alternatively, the management system, or other diagnostic system components, may be "stand-alone" or not coupled directly to a diagnostic system. In such cases, the service platform described herein, and some or all of the service functionality nevertheless may be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 72 and field service units 24 may be linked to service facility 22 via a remote access network 80. For this purpose, any suitable network connection may be employed. Presently preferred network configurations include both proprietary or dedicated networks, as well as open networks, such as the Internet. Data may be exchanged between the diagnostic systems, field service units, and remote service facility 22 in any suitable format, such as in accordance with the Internet Protocol (IP), the Transmission Control Protocol (TCP), or other known protocols. Moreover, certain of the data may be transmitted or formatted via markup languages such as the HyperText Markup Language (HTML), or other standard languages. The presently preferred interface structures and communications components are described in greater detail below.

Within service facility 22, messages, service requests and data are received by communication components as indicated generally at reference numeral 82. Components 82 transmit the service data to a service center processing system, represented generally at reference numeral 84 in FIG. 1. The processing system manages the receipt, handling and transmission of service data to and from the service facility. In general, processing system 84 may include one or a plurality of computers, as well as dedicated hardware or software servers for processing the various service requests and for receiving and transmitting the service data as described more fully below. Service facility 22 also includes a bank of operator workstations 86 which may be staffed by service engineers who address certain service requests and provide off and on-line service to the diagnostic systems in response to the service requests. As described below, problem-solution information exchanges may be completely automated for locating information needed to address specific problems or questions encountered by the user. Also, processing system 84 may be linked to a system of databases or other processing systems 88 at or remote from the service facility 22. Such databases and processing systems form an information library which may include extensive information on operating parameters, best practice, work-arounds, trouble-shooting tips, and so forth, both for particular subscribing scanners, as well as for extended populations of diagnostic equipment. At least one such database preferably includes cross-referenced problems and solutions viewable by the user. As described below, such databases may be employed both for servicing of particular diagnostic systems and for tracking such servicing, as well as for deriving comparison data for use in servicing a particular system or a family of systems.

Figure 2:
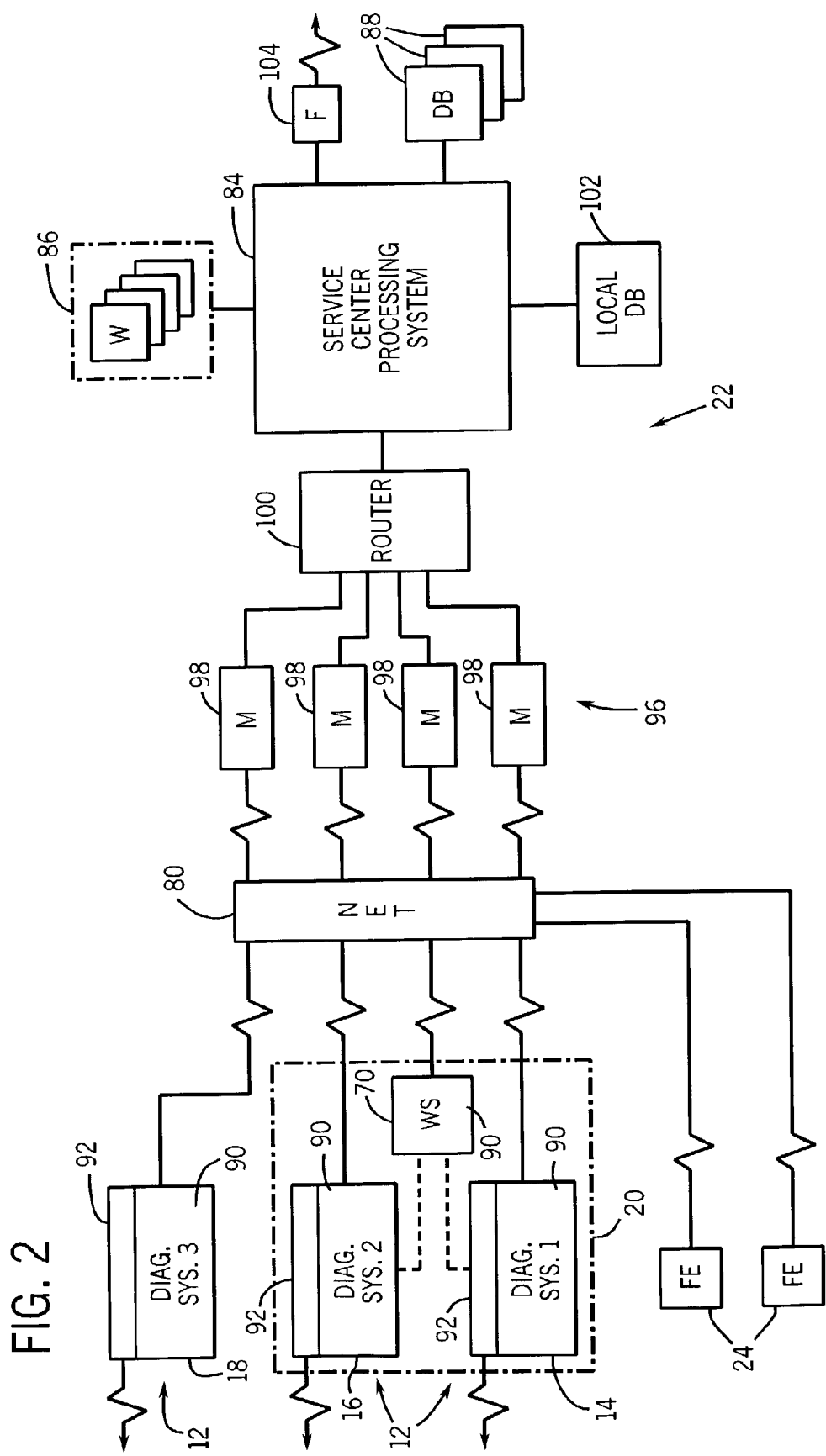
FIG. 2 is a block diagram of the systems shown in FIG. 1 illustrating certain functional components of the diagnostic systems and the service facility.

FIG. 2 is a block diagram illustrating the foregoing system components in a functional view. As shown in FIG. 2, the field service units 24 and the diagnostic systems 12 can be linked to the service facility 22 via a network connection as illustrated generally at reference numeral 80. Within each diagnostic system 12, a uniform service platform 90 is provided. Platform 90, which is described in greater detail below with particular reference to FIG. 3, includes hardware, firmware, and software components adapted for composing service requests, transmitting and receiving service data, establishing network connections and managing financial or subscriber arrangements between diagnostic systems and the service facility. Moreover, the platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access image, log and similar files needed for rendering requested or subscribed services. Where a management station 70 is provided, a similar uniform platform is preferably loaded on the management station to facilitate direct interfacing between the management station and the service facility. In addition to the uniform service platform 90, each diagnostic system is preferably provided with an alternative communications module 92, such as a facsimile transmission module for sending and receiving facsimile messages between the scanner and remote service facilities.

Messages and data transmitted between the diagnostic systems and the service facility traverse a security barrier or "firewall" contained within processing system 84 as discussed below, which prevents unauthorized access to the service facility in a manner generally known in the art. A modem rack 96, including a series of modems 98, receives the incoming data, and transmits outgoing data through a router 100 which manages data traffic between the modems and the service center processing system 84.

As mentioned above, processing system 84 receives and processes the service requests and data, and interfaces with additional service components, both at the service facility and remote from the facility. In the diagram of FIG. 2, operator workstations 86 are coupled to the processing system, as are remote databases or computers 88, including the problem-solution database. In addition, at least one local service database 102 is provided for accessing problem-solution information, verifying license and contract arrangements, storing service record files, log files, and so forth. Moreover, one or more communication modules 104 are linked to processing system 84 to send and receive facsimile transmissions between the service facility and the diagnostic systems or field service units.

Figure 3:
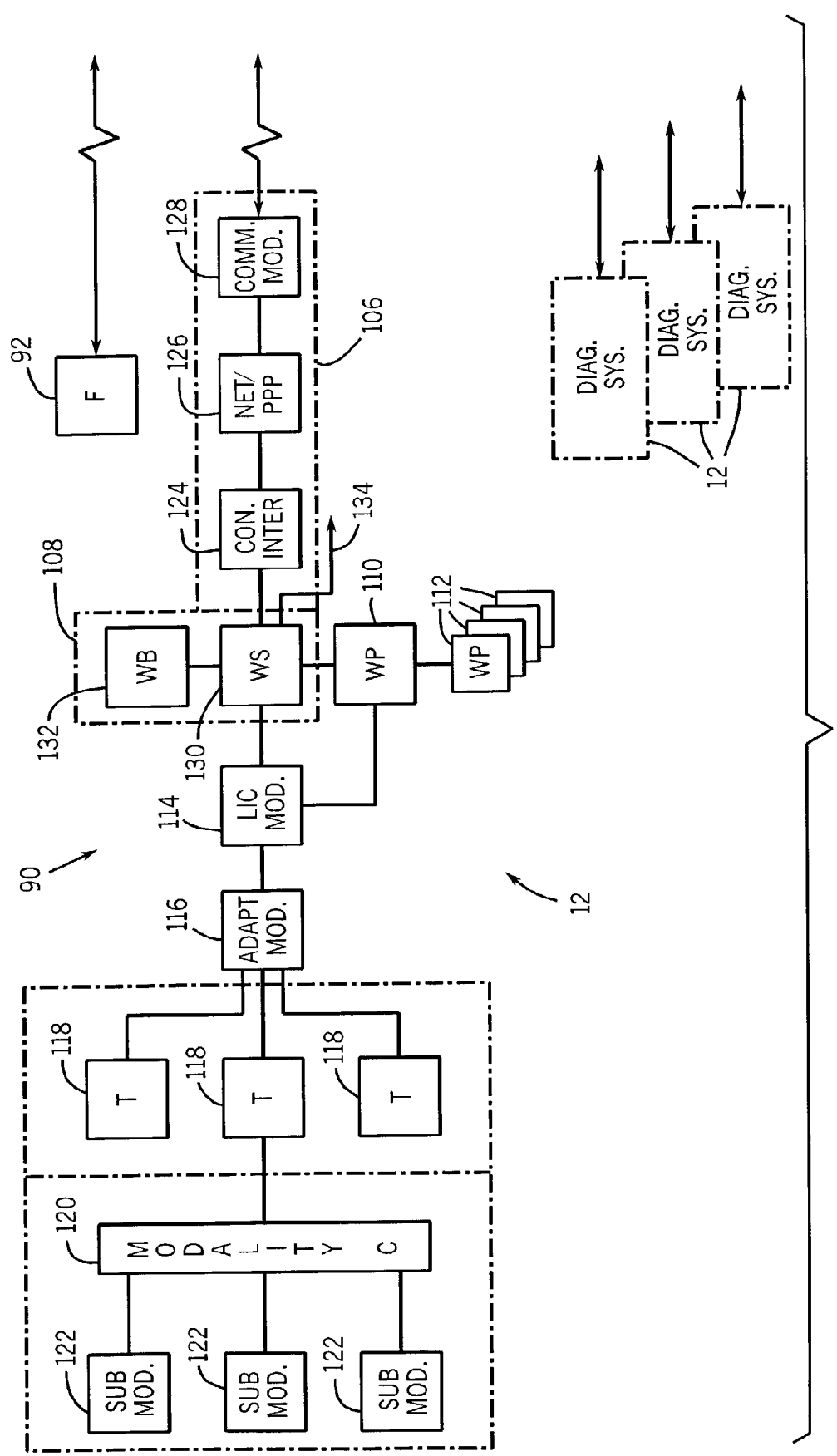
FIG. 3 is a block diagram of certain functional components within a diagnostic system of the type shown in FIG. 1 and FIG. 2 for facilitating interactive remote servicing of the diagnostic system.

FIG. 3 illustrates diagrammatically the various functional components comprising the uniform service platform 90 within each diagnostic system 12. As shown in FIG. 3, the uniform platform includes a device connectivity module 106, as well as a network connectivity module 108. Network connectivity module 108 accesses a main web page 110 which, as mentioned above, is preferably a markup language page, such as an HTML page displayed for the system user on a monitor at the diagnostic system. Main web page 110 is preferably accessible from a normal operating page. Through main web page 110, a series of additional web pages 112 are accessible. Such web pages permit problem queries and service requests to be composed and transmitted to the remote service facility, and facilitate the exchange of problem-solution data, messages, reports, software, protocols, and so forth as described more fully below. It should be noted that as used herein the term "page" includes a user interface screen or similar arrangement which can be viewed by a user of the diagnostic system, such as screens providing graphical or textual representations of data, messages, reports and so forth. Moreover, such pages may be defined by a markup language or a programming language such as Java, perl, java script, or any other suitable language.

Network connectivity module 108 is coupled to a license module 114 for verifying the status of license, fee or contractual subscriptions between the diagnostic system and the service facility. As used herein, the term "subscription" should be understood to include various arrangements, contractual, commercial or otherwise for the provision of services, information, software, and the like, both accompanied with or without payment of a fee. Moreover, the particular arrangements managed by systems as described below may include several different types of subscriptions, including time-expiring arrangements, one-time fee arrangements, and so-called "pay per use" arrangements, to mention but a few.

License module 114 is, in turn, coupled to one or more adapter utilities 116 for interfacing the browser, server, and communications components with modality interface tools 118. In a presently preferred configuration, several such interface tools are provided for exchanging data between the system scanner and the service platform. For example, modality interface tools 118 may include applets or servlets for building modality-specific applications, as well as configuration templates, graphical user interface customization code, and so forth. Adapters 116 may interact with such components, or directly with a modality controller 120 which is coupled to modality-specific subcomponents 122. The modality controller 120 and modality-specific subcomponents 122 will typically include a preconfigured processor or computer for executing examinations, and memory circuitry for storing image data files, log files, error files, and so forth. Adapter 116 may interface with such circuitry to convert the stored data to and from desired protocols, such as between the HyperText Transfer Protocol (HTTP) and DICOM, a medical imaging standard for data presentation. Moreover, transfer of files and data as described below may be performed via any suitable protocol, such as a file transfer protocol (FTP) or other network protocol.

In the illustrated embodiment, device connectivity module 106 includes several components for providing data exchange between the diagnostic system and the remote service facility. In particular, a connectivity service module 124 provides for interfacing with network connectivity module 108. A Point-to-Point Protocol (PPP) module 126 is also provided for transmitting Internet Protocol (IP) packets over remote communication connections. Finally, a modem 128 is provided for receiving and transmitting data between the diagnostic system and the remote service facility. As will be appreciated by those skilled in the art, various other network protocols and components may be employed within device connectivity module 106 for facilitating such data exchange.

Network connectivity module 108 preferably includes a server 130 and a browser 132. Server 130 facilitates data exchange between the diagnostic system and the service facility, and permits a series of web pages 110 and 112 to be viewed via browser 132. In a presently preferred embodiment, server 130 and browser 132 support HTTP applications and the browser supports java applications. Other servers and browsers, or similar software packages may, of course, be employed for exchanging data, service requests, messages, and software between the diagnostic system, the operator and the remote service facility. Finally, a direct network connection 134 may be provided between server 130 and an operator workstation, such as management station 70 within the medical facility (see FIGS. 1 and 2).

In a present embodiment, the components comprising network connectivity module may be configured via an application stored as part of the uniform platform. In particular, a Java application licensed to a service engineer enables the engineer to configure the device connectivity at the diagnostic system to permit it to connect with the service facility. Features of the application are segmented into separate tabbed pages accessible by the service engineer. The application is entered via a license agreement screen. Once accepted, the service engineer can configure parameters of the system modem, the schedule for running automatic diagnostic checks, and establish electronic messaging, such as for automatic service report generation. Once the modem is configured, the service engineer establishes contact with the service facility and provides data enabling the service facility to download any remaining data needed for secure communication between the system and the service center. Upon exit from the application, a configuration status is presented to the service engineer, including status of an automatic test of connectivity between the sites.

Figure 4:
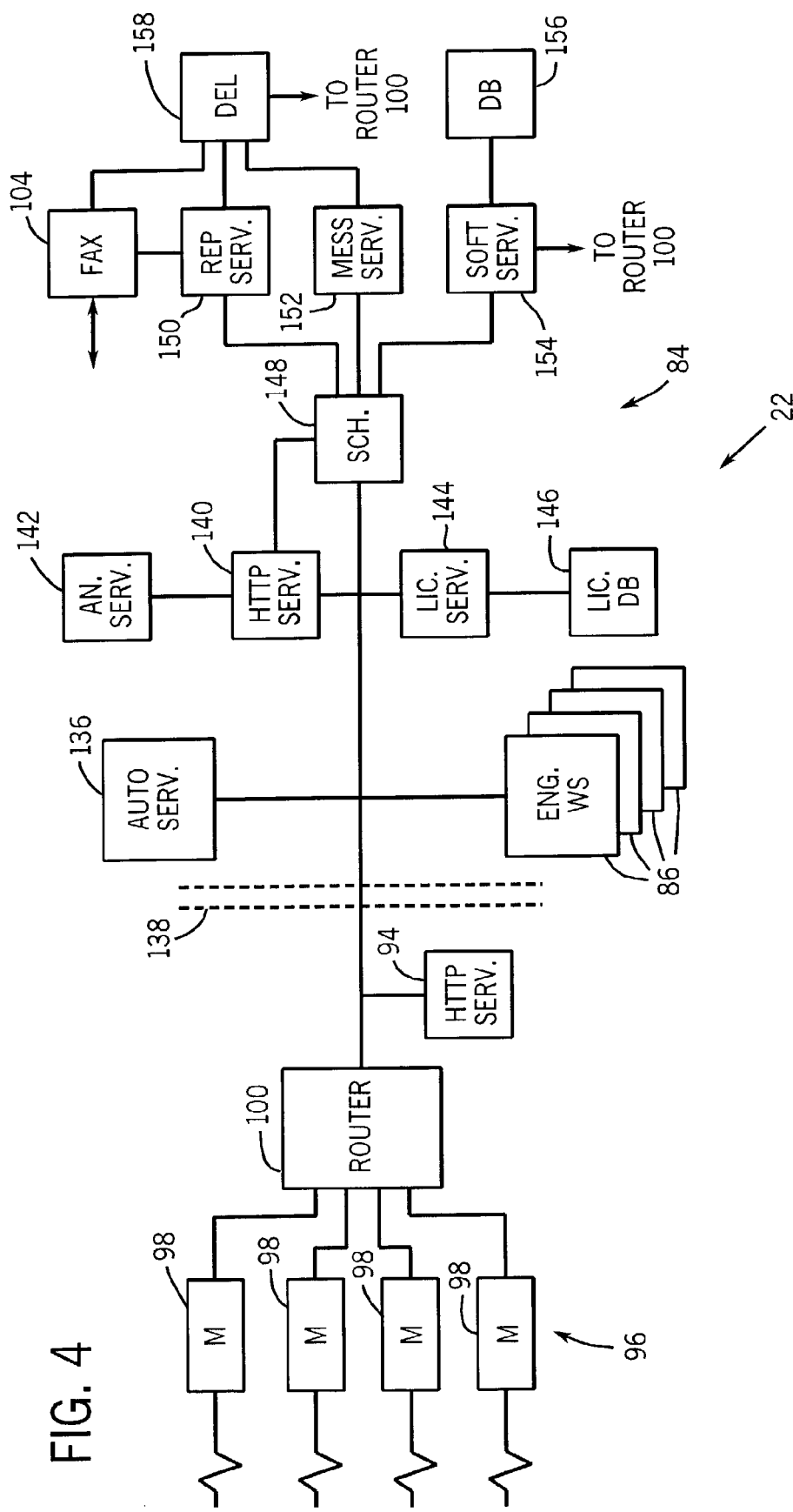
FIG. 4 is a block diagram of certain of the functional components of the service facility illustrated in FIG. 1 and FIG. 2 for rendering interactive remote service to a plurality of medical diagnostic systems.

FIG. 4 illustrates exemplary functional components for service facility 22. As indicated above, service facility 22 includes a modem rack 96 comprising a plurality of modems 98 coupled to a router 100 for coordinating data communications with the service facility. An HTTP service server 94 receives and directs incoming and outgoing transactions with the facility. Server 94 is coupled to the other components of the facility through a firewall 138 for system security. Operator workstations 86 are coupled to the port manager for handling service requests and transmitting messages and reports in response to such requests. An automated service unit 136 may also be included in the service facility for automatically responding to certain service requests, sweeping subscribing diagnostic systems for operational parameter data, and so forth, as described below. In a presently preferred embodiment, the automated service unit may operate independently of or in conjunction with the interactive service components comprising processing system 84. It should be noted that other network or communications schemes may be provided for enabling the service facility to communicate and exchange data and messages with diagnostic systems and remote service units, such as systems including outside Internet service providers (ISP's), virtual private networks (VPN's) and so forth.

Behind firewall 138, an HTTP application server 140 coordinates handling of service requests, messaging, reporting, software transfers and so forth. Other servers may be coupled to HTTP server 140, such as service analysis servers 142 configured to address specific types of service requests, as described more fully below. In the illustrated embodiment, processing system 84 also includes a license server 144 which is coupled to a license database 146 for storing, updating and verifying the status of diagnostic system service subscriptions. Alternatively, where desired, license server 144 may be placed outside of fire wall 138 to verify subscription status prior to admission to the service facility.

Handling of service requests, messaging, and reporting is further coordinated by a scheduler module 148 coupled to HTTP server 140. Scheduler module 148 coordinates activities of other servers comprising the processing system, such as a report server 150, a message server 152, and a software download server 154. As will be appreciated by those skilled in the art, servers 150, 152 and 154 are coupled to memory devices (not shown) for storing data such as addresses, log files, message and report files, applications software, and so forth. In particular, as illustrated in FIG. 4, software server 154 is coupled via one or more data channels to a storage device 156 for containing transmittable software packages which may be sent directly to the diagnostic systems, accessed by the diagnostic systems, or supplied on pay-per-use or purchase basis. Message and report servers 152 and 154 are further coupled, along with communications module 104, to a delivery handling module 158, which is configured to receive outgoing messages, insure proper connectivity with diagnostic systems, and coordinate transmission of the messages.

Figure 5:
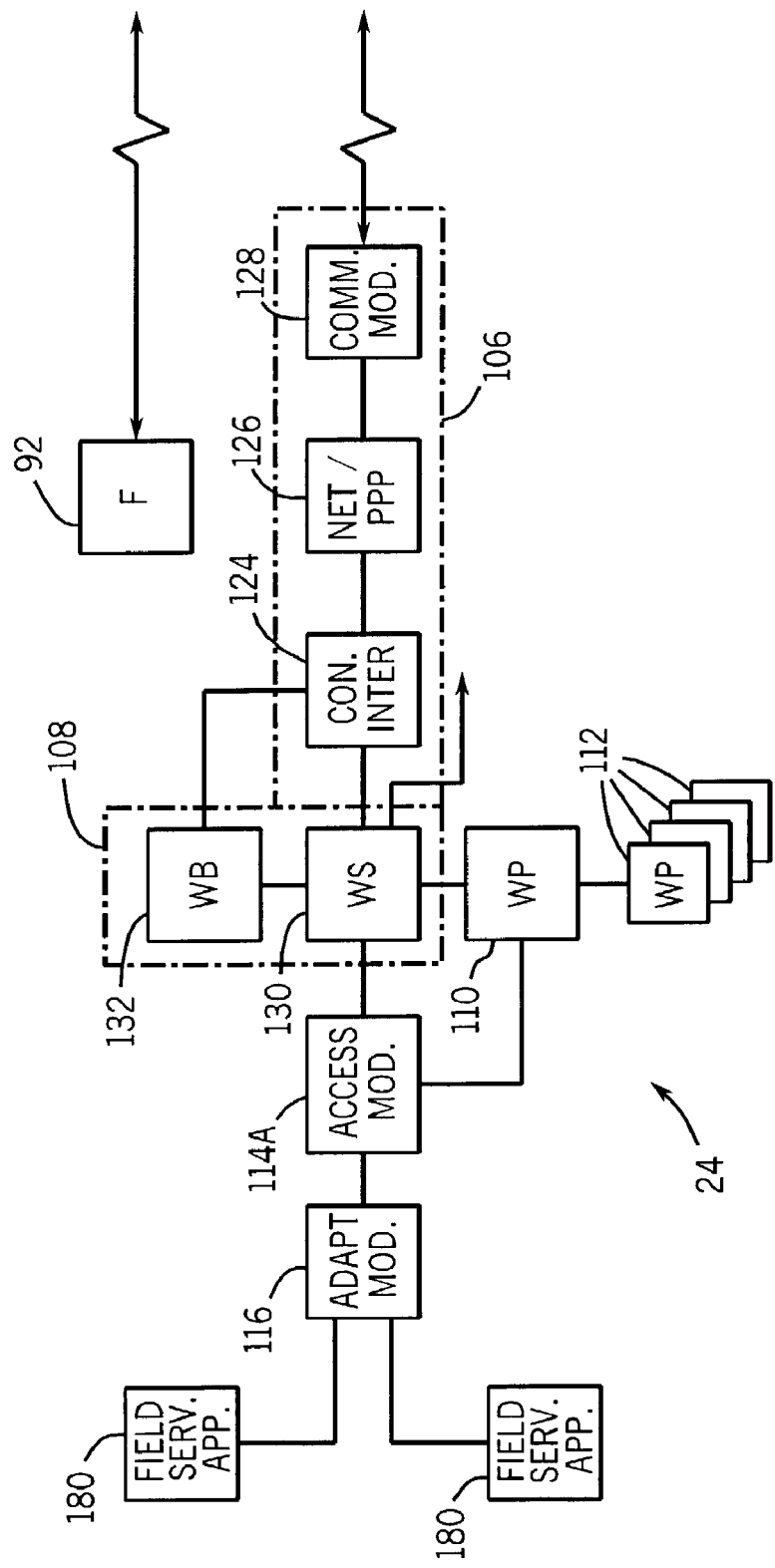
FIG. 5 is a block diagram of functional components within a field service unit which can be coupled to the diagnostic systems and to the service facility for exchanging service information with a field service engineer.

FIG. 5 illustrates certain of the functional components contained within an exemplary field service unit 24. Field service unit 24 may include a portable computer designed for use by remote service engineers. The unit includes a service platform which includes certain functional circuitry for establishing a uniform service base as discussed above for the diagnostic systems themselves. Moreover, the service units include specific service tools which enable the field engineer to request and receive remote service messages, reports on specific diagnostic systems, service schedules, and so forth. Through the service platform, therefore, the field engineer may access system configurations, historic log information, system network information, analysis logs and data, and so forth. In addition, the field service unit described below, in conjunction with the system platform and the service facility components, permits such information to be accessed either by the field engineer on the field service unit, or at the diagnostic system itself (e.g. when the service engineer is on-site), or from the remote service facility. The field engineer may also update service records either from the field service unit or from the diagnostic system, as desired.

Thus, as shown in FIG. 5, an exemplary field service unit includes a device connectivity module 106 and a network connectivity module 108. Device connectivity module 106 may include connectivity interface circuitry 124, a network or PPP module 126, and a modem 128, as described above for the diagnostic system with reference to FIG. 3. The network connectivity module 108 may, in turn, include a server 130 and browser 132 substantially identical to those of the diagnostic systems, enabling the field engineer to receive, view and compose messages, reports, and so forth via a main web page 110 and a series of web pages 112. Moreover, an access module 114A is provided for allowing the service facility to verify the license and security status of the field service unit. For example, the access module, in cooperation with circuitry at the service facility, may permit a field service engineer to access data or applications providing some or all of the functionality offered to service engineers at the service facility. Such functionalities may be similar to those provided at the diagnostic systems themselves, or may offer the service engineer a wider range of service options. One or more adapter modules 116 provide for interfacing the network circuitry with various field service tools. In particular, the field service unit may be equipped with service applications, as indicated at blocks 180, such as for analyzing diagnostic system performance data, scheduling regular or special service calls, scheduling for shipment of replacement parts, and so forth. Other service applications may include applications generally similar to those executed on the operator workstations 86 of the service facility (see, e.g. FIG. 4). Such applications may permit the field service engineer to address service requests at the diagnostic system site, or remote from the site as required, and transmit service messages and updates via the remote field service unit.

In a presently preferred embodiment, the foregoing functional circuitry may be configured as hardware, firmware, or software on any appropriate computer platform. For example, the functional circuitry of the diagnostic systems may be programmed as appropriate code in a personnel computer or workstation either incorporated entirely in or added to the system scanner. The functional circuitry of the service facility may include additional personal computers or workstations, in addition to a main frame computer in which one or more of the servers, the scheduler, and so forth, are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of service data between the diagnostic systems and a remote service facility, which is preferably implemented in an interactive manner to provide regular updates to the diagnostic systems of service activities.

As described above, both the diagnostic systems and the field service units preferably facilitate interfacing between a variety of diagnostic system modalities and the remote service facility via a series of interactive user-viewable pages. FIGS. 6 through 10 illustrate exemplary pages for providing interactive information, composing service requests and problem queries, selecting and transferring messages, reports and diagnostic system software, and so forth. It should be noted that through the following discussion, reference is made to viewable pages for interfacing in the language of the present description. However, in a presently preferred embodiment, the platform may be configured to present such interface pages in several different languages, depending upon the country in which the system is installed.

Figure 6:
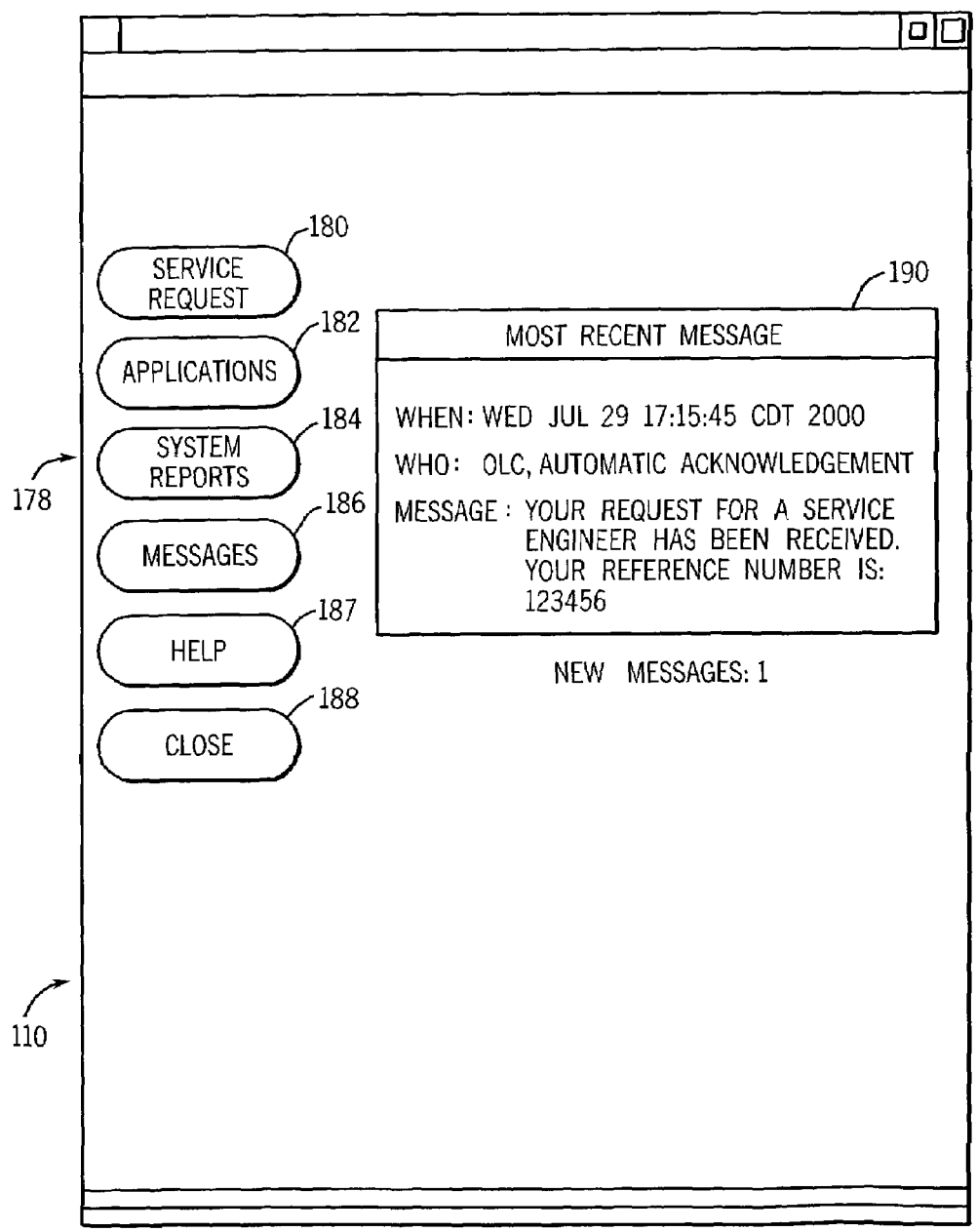
FIG. 6 is an exemplary user interface page incorporated in the diagnostic system for placing service requests, and sending and receiving service data between the diagnostic system and a remote service facility.

As illustrated first in FIG. 6, a main web page 110 is accessible from a normal diagnostic system screen viewable on the diagnostic system monitor 36, 52 or 66. Main web page 110 may therefore be viewable by clicking an input device such as a mouse on an icon (not shown) on the normal operational screen. Main web page 110 includes a series of navigation devices 178 in the form of graphical buttons for accessing other interface pages in the graphical user interface. In the illustrated embodiment, these graphical devices include a service request button 180 for accessing a service request page, an applications button 182 for accessing an applications page, a system reports button 184 for accessing service reports, and a messages button 186 for sending and receiving interactive service messages. A help button 187 is provided for accessing user information, help topics and so forth, which may be resident on the system. A close or exit button 188 is provided for returning to the normal scanner interface page. In addition to these navigational devices, main page 110 includes a message area 190 in which information regarding the most recent messages is displayed. This information may include identification of the time and date received, the originator of the message, and a brief summary of the message content or title. Thus, upon accessing main page 110, the system user is made aware of service activities carried out by the remote service facility or field service engineer.

Figure 7:
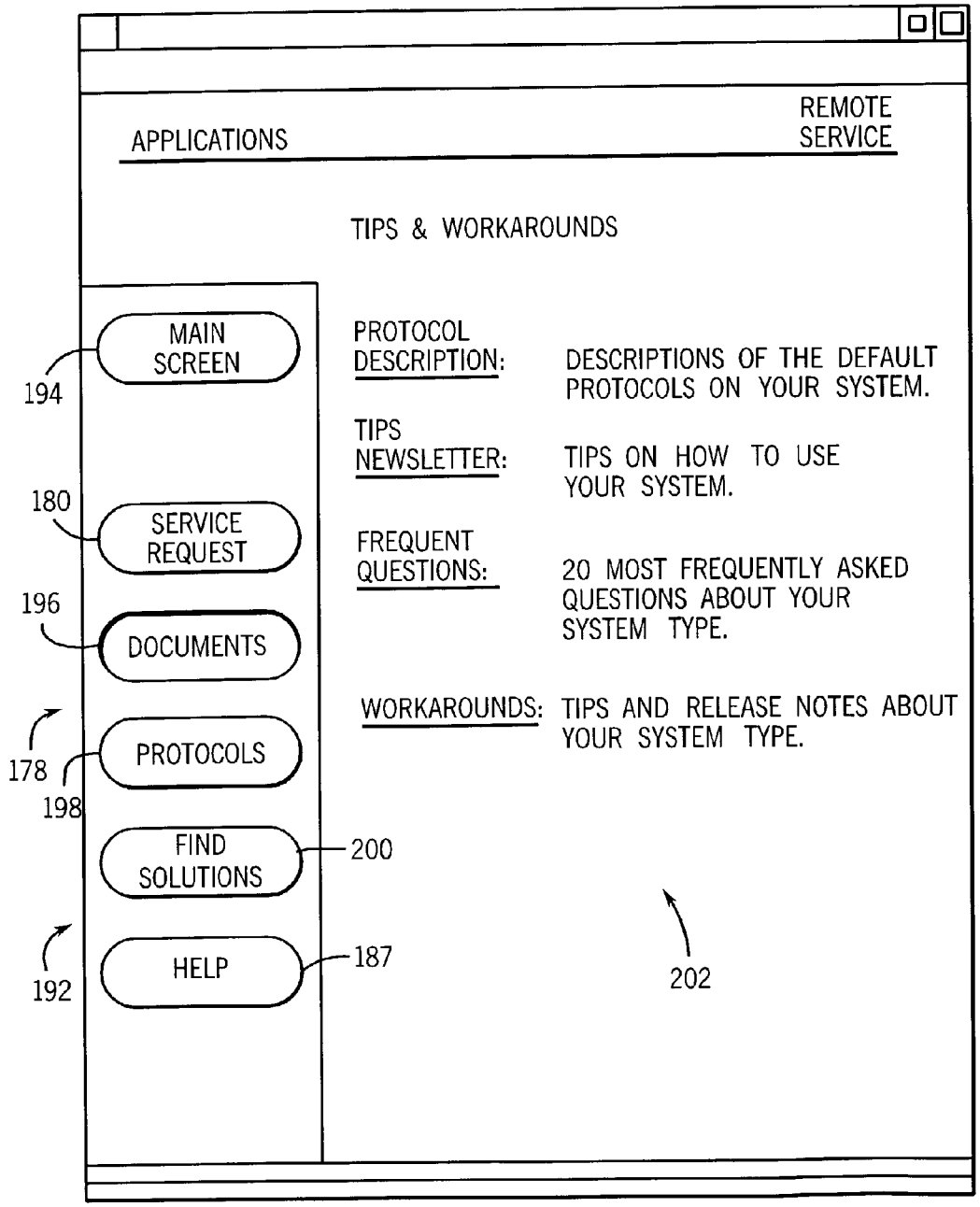
FIG. 7 is a second user interface page for conveying service information to the scanner operator from the service facility.

FIG. 7 illustrates the applications page 192 accessed by actuation of the applications button 182 in the main page. As in the main page, the applications page 192 includes a series of graphical buttons 178 for navigating through the other pages of the graphical user interface, including a main screen button 194 for returning to the main screen shown in FIG. 6. A "snap shot" or current system state may be captured as the basis for the service request. The service request page would be accessed from the normal operating page at the scanner, through the service request button 180 in the main web page or one of the other web pages. With the system state remaining at its condition just prior to accessing the service request page, image data files, log files, error files, and so forth may be identified, captured, stored and transmitted to the service facility for evaluation of potential problems in the diagnostic system. As will be appreciated by those skilled in the art, the service request therefore enables the user to identify potential imaging system difficulties that may not be apparent in subsequent examinations, or may not recur on a predictable basis. It should be noted that the service requests formulated via service request button 180 are not limited to identifying image acquisition or processing problems, or to capturing image files only. Such requests may relate to general or system-specific questions, or may identify data files containing system configuration data, and data indicative of historical operational parameters or events. Such events may include parameter limits exceeded, timeouts, protocol configurations, hardware and software configurations, work queues, and so forth. Similarly, image data identified for evaluation may include both processed, partially processed and raw data from which images are subsequently reconstructed.

Additional web pages may be accessible through the applications page 192, such as a documentation or a help page or series of pages, accessible through a graphical button 196. A protocols page is accessible through a graphical button 198. A queries page for searching the service facility library for solutions to questions is accessible through a graphical button 200. This or a similar button or other access device may be provided for accessing the most frequently referenced problem-solution combinations (e.g. "top ten") which, as mentioned above, may be specifically tailored to the scanner, imaging (or image management) system. Moreover, page 192 is provided with a text area 202, in which text describing various service documentation, messages, modality equipment, operational instructions, and so forth may be displayed.

It should be noted that in a presently preferred configuration, the information displayed within text area 202 is specifically designed for the particular modality and type of diagnostic system on which the uniform platform is installed. As described below, when the service center is placed into network contact with the diagnostic system, identification of the diagnostic system to the service center allows the service center to transmit and display modality-specific information in the text area. In the embodiment illustrated in FIG. 7, such text may include information on imaging protocol or examination descriptions, a system newsletter specifically adapted for the modality and system type, up-to-date frequently asked questions and answers, and instructional suggestions for operation of the diagnostic system. The user can access the specific information described in the text area by selection of all or a portion of the text describing the topic. In the presently preferred embodiment, the accessed information may be stored in local memory devices within the diagnostic system, or selection of the text may result in loading of a uniform resource locator (URL) for accessing a remote computer or server via a network link.

Figure 8:
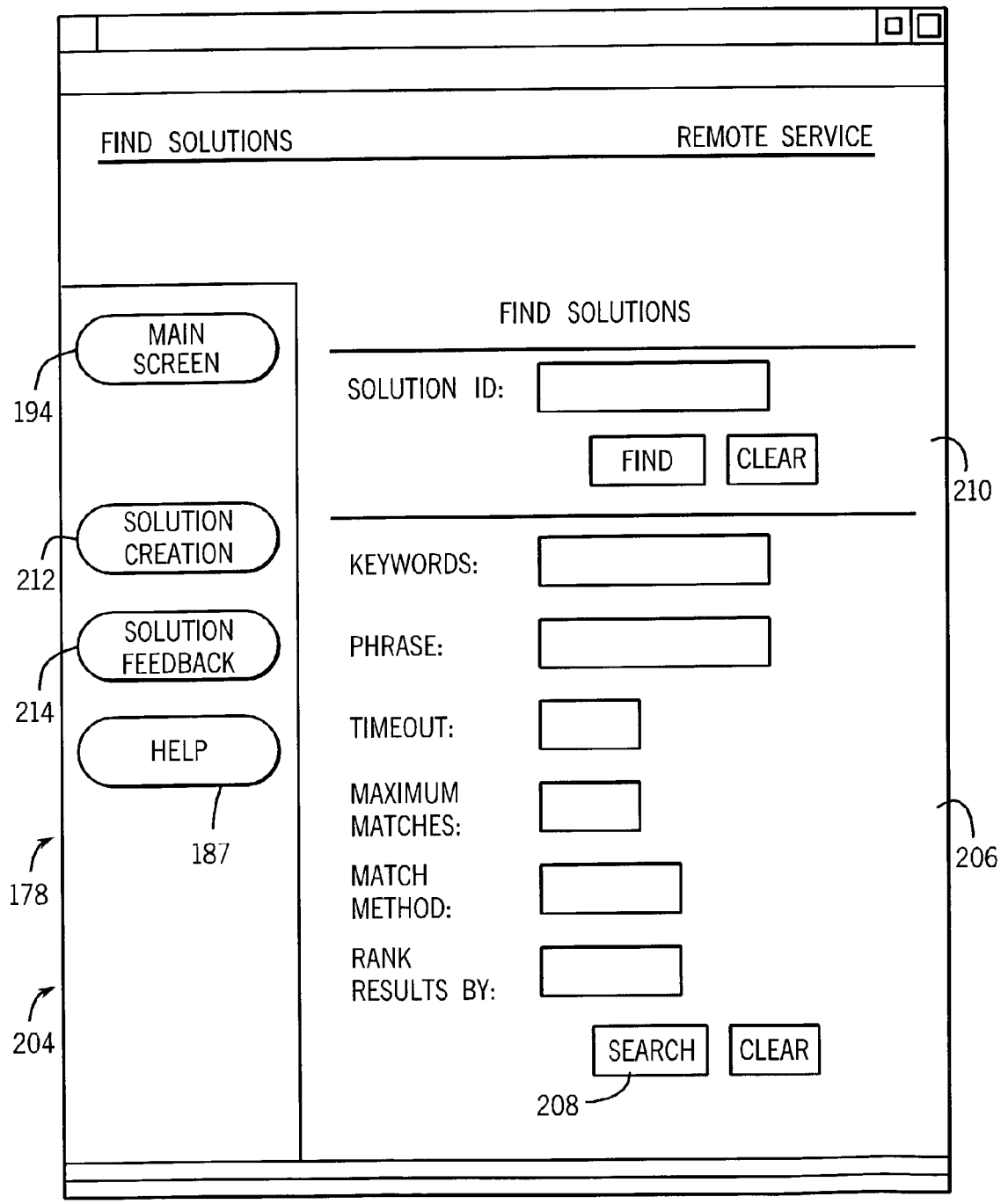
FIG. 8 is an interface page for generating a problem query at the scanner and for conveying the query to the service facility.

As mentioned above, the uniform graphical user interface facilitates formulation of queries and enables scanner operators to search the service facility library in a similar manner across several diagnostic system modalities. FIG. 8 illustrates an exemplary interface page for formulating such queries. In the query formulation page shown in FIG. 8, an area 206 is provided for entering key words or phrases of the query as well as other search criteria. For example, a user can specify a time out period, in addition to a method for matching results with the query, that is whether each search result must contain all of the key words and phrases specified in the query or only one of them. In addition, the user can specify a maximum number of matches to be retrieved and an order in which the results should be ranked. The user can transmit a query to the service facility center by clicking via an input device such as a mouse on a graphical search button 208. It should be noted that the server included in the uniform platform includes unique system identification data which may supplement the information input by the user. It should also be noted that the fields illustrated in FIG. 8 are not exhaustive. Other, more, or fewer input fields may be processed as desired.

Query formulation page 204 also includes another area 210 (not generally viewable or accessible by the user) which enables a service engineer to search the service facility library by a particular solution identification number. In addition, service engineers may enter new solutions into the library at a solution creation page, accessible through a graphical button 212, or provide feedback on solutions already in the library through a solution feedback page, accessible by a graphical button 214. Again, in a presently preferred embodiment, area 210 and graphical buttons 212 and 214 are generally not available to scanner operators at diagnostic systems, but rather only available to service engineers for the purpose of updating the library.

Figure 9:
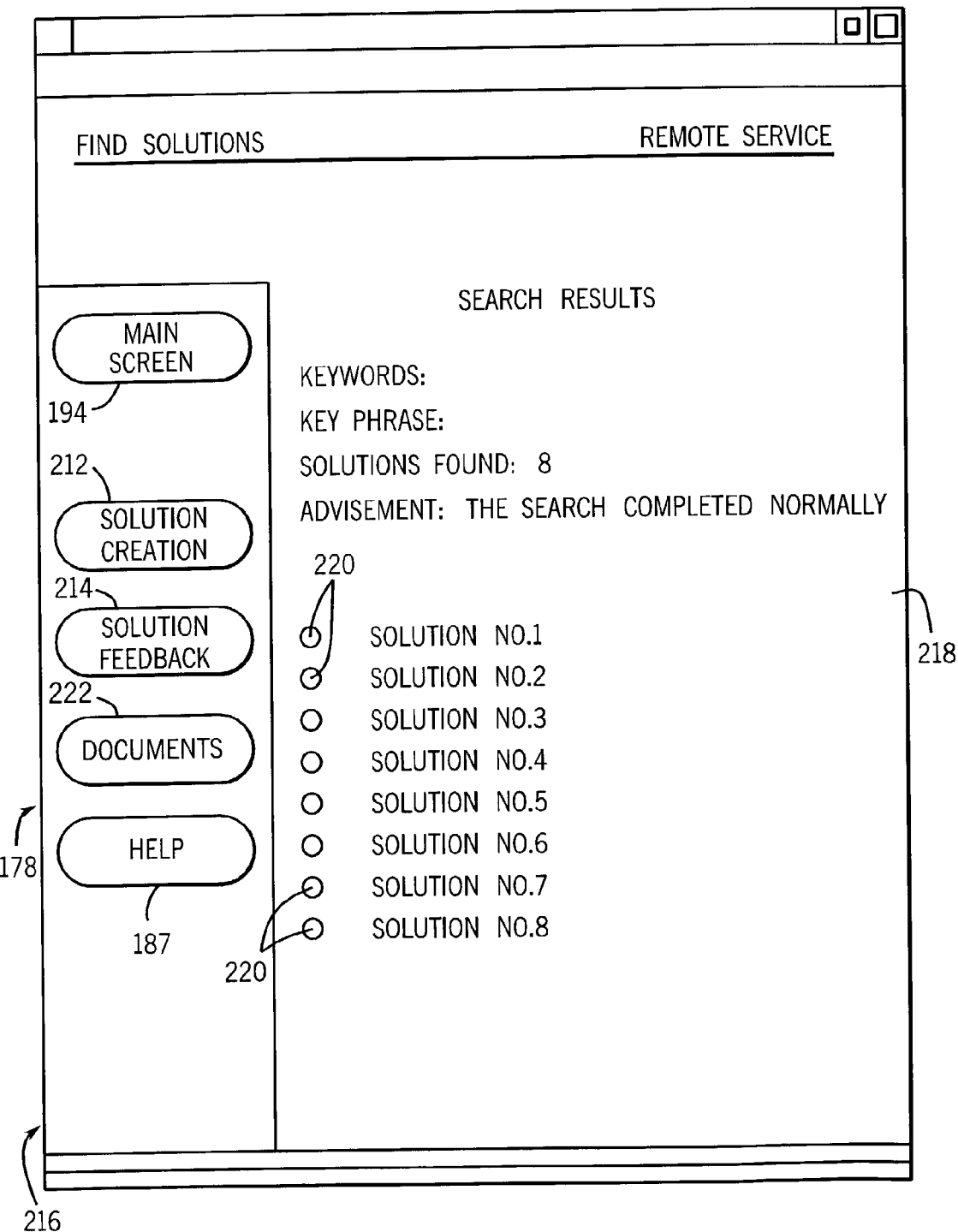
FIG. 9 is an interface page for displaying a list of search results provided by the service facility to the scanner.

FIG. 9 illustrates an interface page 216 for informing the system operator of the search results. The search results page 216 includes a text area 218 which summarizes the key words and phrases that the user entered for the search as well as the number solutions located and the status of the search. In addition, the search results page 216 includes a series of graphical or access devices or links 220, each associated with a particular solution to the problem query. In the exemplary search results page shown in FIG. 9, the search successfully located eight solutions. Any number of solutions may be associated with a particular query. Because information identifying the diagnostic system is transmitted to the service center when the system is placed into network contact with the service center, the search results displayed at the diagnostic system are specific to the system modality. Thus, a search for a query entered at a CT system will locate only CT-specific information, while another query entered at an MRI system will result in only MRI-specific information. On the contrary, where desired, the present technique may permit various types of information to be accessed from a single station, particularly from a management work station, PC or the like in a radiology department, institution or elsewhere. One skilled in the art will appreciate that this information may be further tailored to a particular system model. As described in greater detail below, new or additional solutions may be added to the listing from time to time. By clicking on a particular graphical solution link 220, the user can access that solution page to obtain detailed information about that solution.

Figure 10:
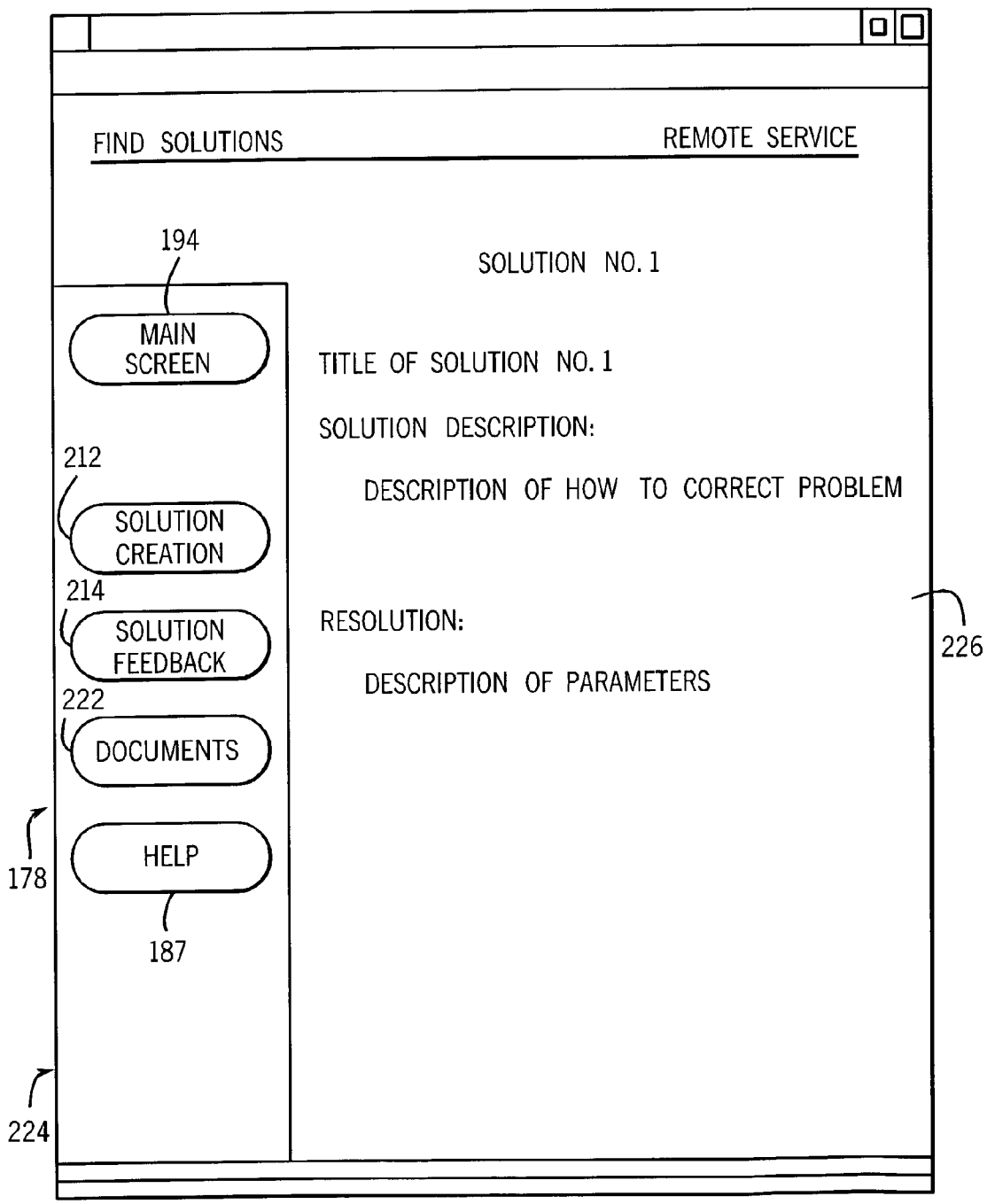
FIG. 10 is an interface page for displaying at the scanner details of a particular solution from the list.

FIG. 10 illustrates an interface page for displaying information about a particular solution. Solution page 224 is accessible through the search results page shown in FIG. 9. Upon accessing solution page 224, the system user is provided with detailed information about the solution. This information is provided in a text area 226, which may include a title of the solution, its description, and various configuration parameters. Links to other information, actions, services, and so forth may be provided by selectable text or a graphical device 222 on solutions page 224 to facilitate access to additional information. Moreover, graphical buttons or other links, such as those shown in FIG. 7, may also be displayed and accessible from the pages shown in FIGS. 9 and 10.

Figure 11:
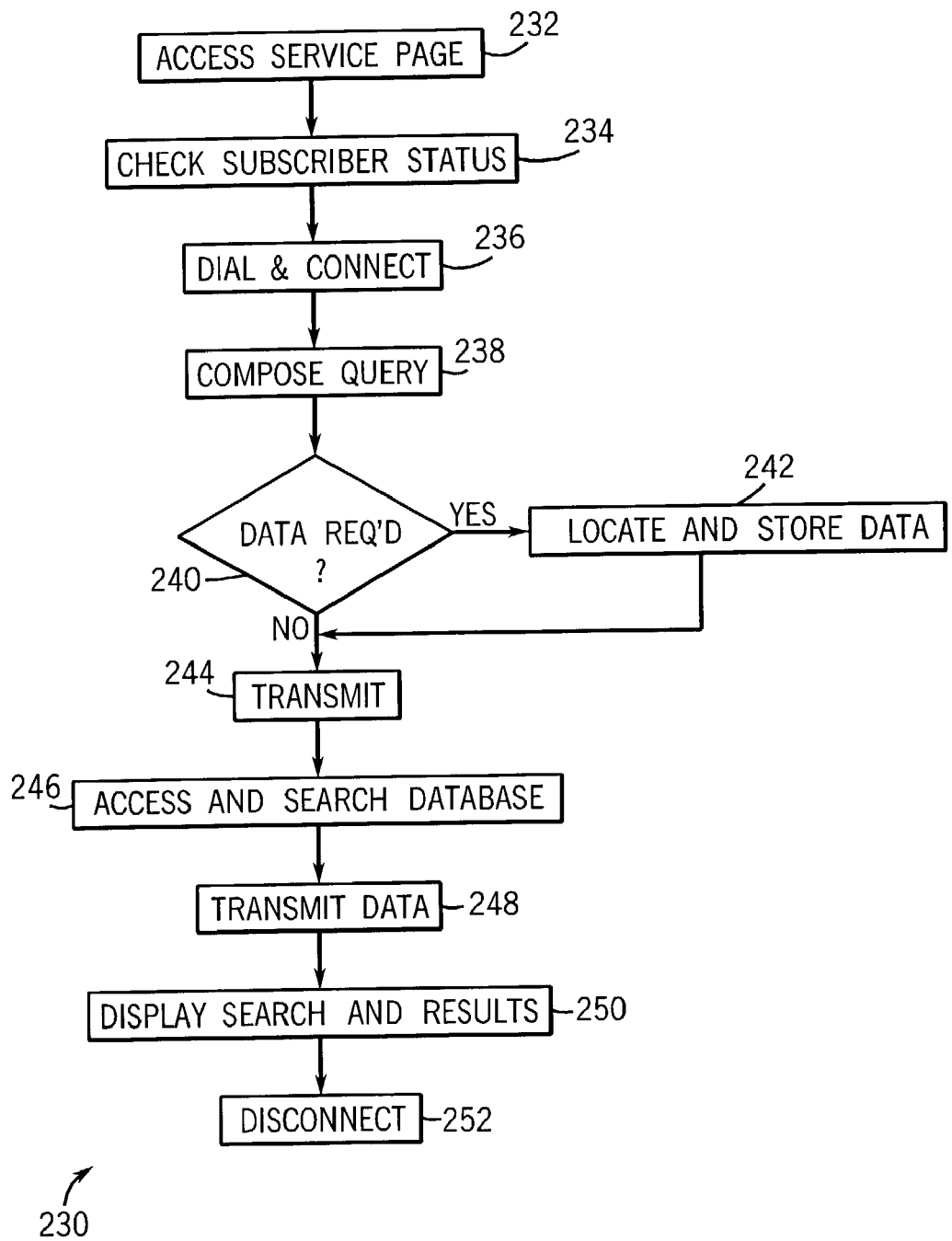
FIG. 11 is a flow chart illustrating exemplary logic implemented by the diagnostic systems for requesting one type of service from the remote service facility.
Figure 12:
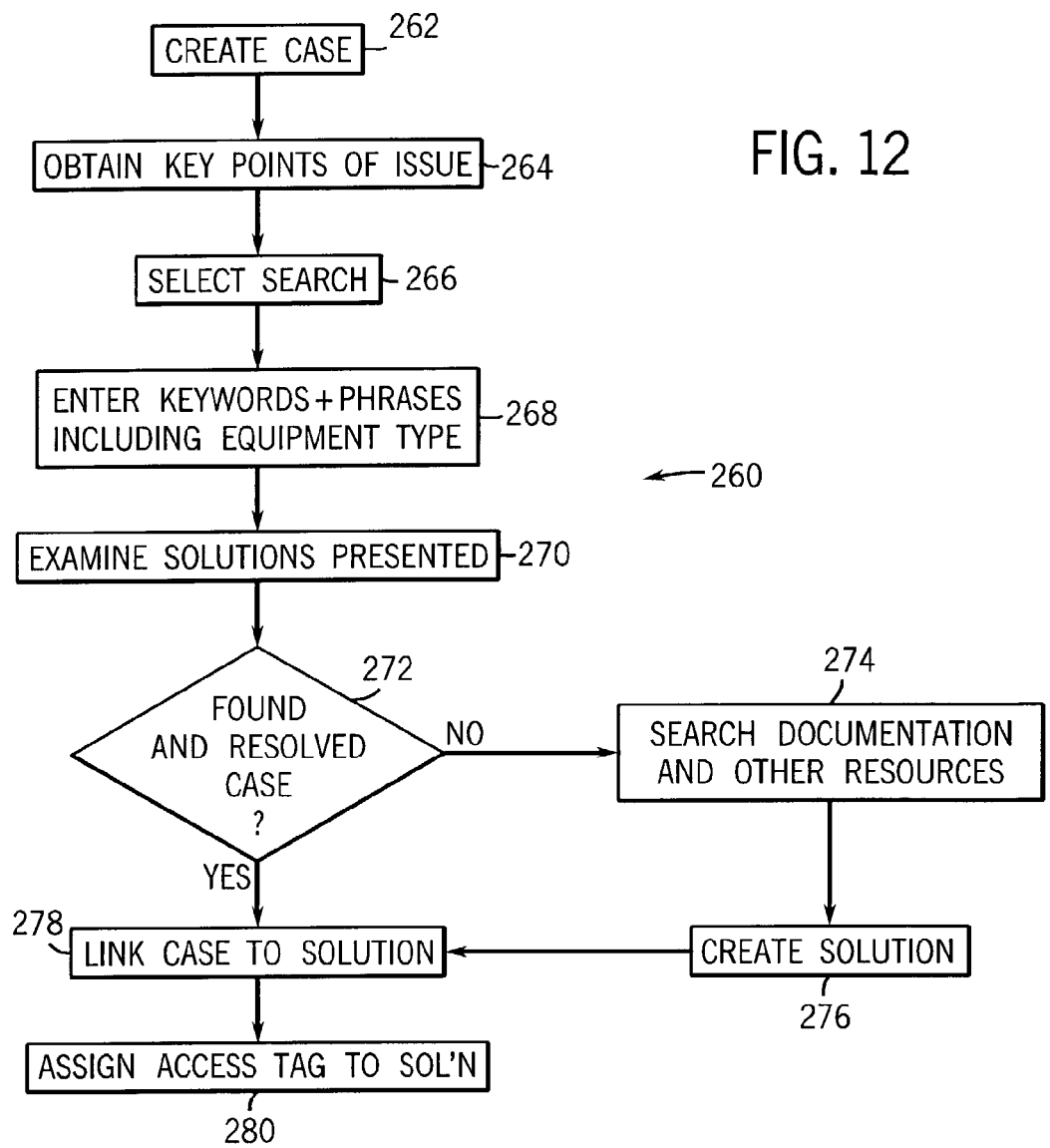
FIG. 12 is a flow chart illustrating exemplary logic implemented by the service facility in updating the service facility library.

FIGS. 11 and 12 illustrate exemplary control logic implemented by the functional components described above at the diagnostic systems, the service facility, and remote field service units. In particular, FIG. 11 illustrates exemplary logic for composing and transmitting a query via the graphical user interface and uniform platform. The control logic, indicated generally by reference numeral 230, begins at step 232, wherein a service page such as the find solutions page shown in FIG. 8 is accessed from a normal operating page at the diagnostic system or at a management station. The logical steps illustrated in FIG. 11 are particularly adapted for searching problem queries of a general nature related to diagnostic systems or queries as to particular applications and the like. At step 234 the diagnostic system may verify a subscriber status required for the requested service. In particular, the various service requests may be categorized by type, and associated with specific contract types, subscriber services, licenses, and so forth. Such subscriber data will be stored in a license module such as module 114 shown in FIG. 3. Where the service requests are freely made by the scanner, this step may be eliminated. However, where specific service subscriptions are required, a comparison is made at step 234 between the required contractual arrangement or subscriber license and the similar information on file for the diagnostic system. If the subscriber status is valid, then at step 236, the diagnostic system connectivity module dials and connects the diagnostic system to the service facility. At step 238, the query is composed when the system user enters key words or phrases related to a question or problem. The user may also enter other information, such as those as described above with respect to FIG. 8.

At step 240 the diagnostic system server 130 (see FIG. 3) determines the type and location of data that may be required for addressing the query. This data preferably includes an identification of the system and/or system configuration to facilitate addressing the inquiry, such as to provide system-specific solutions. Also, certain queries may require information regarding imaging sequences, acquired image data files may be identified, along with scanner log files, error files, and so forth. More particularly, the data identified (and later transmitted if required) may include both raw and processed image data, software configuration information, systems data (e.g. hardware and software identification and configuration), and so forth. Certain of the data may be specific to the modality of the system (such as data in a DICOM format), and may be defined by modality through adaptation of the uniform platform via the modality interface components. Where such data is required for properly addressing the service request, the data files are located as indicated at step 242. The files may be backed up or stored from the modality-specific circuitry through the intermediary of adapter modules, such as adapter module 116 (see FIG. 3). These steps in the exemplary logic therefore permit the user to configure a query which effectively captures a state of the diagnostic system which gave rise to the inquiry. The query may be thereby linked to the specific problem for which service is needed.

At step 244 the query is transmitted to the service facility. Information, which may also be transmitted with the query, includes identification of the diagnostic system, a facility in which the system is located, and so forth. It should be noted that in the preferred embodiment, the query is stripped of information relating to specific patient identifications. Other data, such as financial or account information may be included with the message or may similarly be stripped from the query.

At step 246 the service facility processing system accesses and searches its library based on the key words and phrases specified in the query as well as the accompanying system information. The search results in a list of information that is specific to the particular system modality. It should be noted that the service facility library is vast and may include information pertaining to a plurality of system modalities. As will be described in greater detail below, the information available to any one diagnostic system is only a subset of the information contained in the library and available to the service engineers.

At step 248 data resulting from the search are then transmitted to back to the diagnostic system. A portion or all of the data may be transmitted by the service facility to the diagnostic system, management system, or other user device submitting the inquiry. Alternatively, transmission of all or some of the data may be delayed until a subsequent connection session. At step 250 the search results are displayed to the system operator at a search results page similar to that shown in FIG. 9. From there the operator can access any or all of the solutions listed on the search results page as shown in FIG. 10. In addition, the operator may access additional information or take actions via links 222 or similar devices. At step 252 the diagnostic system may disconnect from the service facility. In the alternative, additional queries, service requests, and so forth may be transmitted, or other remote activities may be performed at this stage. When certain of the data required to address the query is not transmitted immediately, the service facility may recontact the medical diagnostic system at a subsequent time.

In general, query responses will vary depending upon the tenor of the query. For example, the response may include suggestions for operating the diagnostic system or a medical institution in which the system is installed. Such information may provide "best practices" type information for the particular system type or modality, as well as instructional information on user or care for the system. The information may also include notices, such as for anticipated service needs, scheduled or available training sessions and so forth. The response may further include programs or protocols or reports of system operation.

FIG. 12 illustrates steps in exemplary control logic for updating problem and solution information contained in the service facility library. This library updating logic, indicated generally by reference numeral 260, begins at step 262 with the creation of a case. A case may arise when a system operator contacts a service engineer with a particular question or problem. At step 264 the service engineer determines the key points of issue which need resolution.

At step 266, the service engineer then selects an appropriate search. Along with the search, the service engineer enters at step 268 information, such as system modality and model, key words and phrases, and so forth. The processing system will search the entire service facility library, including information not accessible by the diagnostic system, for solutions to the search. At step 270, the system engineer will examine the solutions presented to determine whether any of the solutions is related to the case. If at step 272, the service engineer determines that none of the solutions found resolves the issue presented by the case, the engineer will proceed to step 274 and search other documentation and other resources to locate the appropriate solution. At step 276, the service engineer will create an appropriate solution based on the information located at step 274. The solution may then be submitted for review and approval. Once the solution has been approved, the newly-created solution and case are linked together.

On the other hand, if at step 272 the service engineer determines that the search has found an appropriate solution to the case, the engineer at step 278 will link the case to the solution. Service engineers can link additional solutions to a particular case problem by entering the solution at a solution creation page, accessible by graphical button 212 shown in FIGS. 8 through 10. The solution creation page enables system engineers to update the problem and solution information stored in the library.

Finally, at step 280 the service engineer may assign an access tag to the case problem and solution. The access tag indicates whether the information may be accessible by diagnostic systems, management systems, or other users, or is only accessible by service engineers. The service facility library may include information relating to populations of diagnostic systems, new or updated routines, protocols, instructional documentation and courses, schedules for training, and so forth, not all of which are appropriate for diagnostic system operators. Information deemed accessible by diagnostic systems may include frequently asked questions as well as application-related questions and answers. Thus, by marking with the appropriate access tag the subset of information available to the diagnostic systems, the service facility can restrict access to its library and reduce the volume of data which the must be searched in response to a systems operator query.

As noted above, the interactive nature of the present invention enables a system operator to quickly obtain answers to a wide range of questions, ranging from those of a general nature to those directed at a particular application of the diagnostic system. The system operator can access the service facility library and search a subset of the information contained in the library for topics applicable to the particular diagnostic system. In addition, the present invention enables a service facility to store in its central library of databases information pertaining to a number of medical diagnostic system modalities. This information can be easily updated and efficiently distributed to the appropriate diagnostic systems.

The invention claimed is:

1. A method for providing problem and solution information to medical diagnostic systems, the method comprising:
   storing information on a machine readable medium, the information including a plurality of problems and a plurality of solutions, each problem being associated with at least one solution;
   displaying user viewable indicia at a medical diagnostic location, the indicia being representative of a description of at least one solution of interest in response to a respective problem; and
   loading the at least one solution of interest at the medical diagnostic location from the machine readable medium.

2. The method of claim 1, wherein the machine readable medium includes a memory device remote from the medical diagnostic location.

3. The method of claim 2, wherein the information accessible by the medical diagnostic location is a subset of the information stored in the memory device.

4. The method of claim 3, further comprising assigning an access tag to each of the plurality of problems, wherein the access tags identify the subset of information accessible by the medical diagnostic location.

5. The method of claim 1, further comprising:
   configuring a problem query at the medical diagnostic location; and
   transmitting the query to a remote location of the machine readable medium,
   wherein the at least one solution is displayed in response to the query.

6. The method of claim 1, further comprising verifying a subscription status for the medical diagnostic location prior to loading the at least one solution.

7. The method of claim 6, further comprising transmitting an authorization prompt to the medical diagnostic location based upon the verification of the subscription status.

8. The method of claim 1, further comprising:
   accessing product configuration data representative of a hardware or software configuration of the medical diagnostic system; and
   displaying the indicia based upon the configuration data.

9. The method of claim 1, further comprising adding a new problem and a respective solution to the information on the machine readable medium.

10. The method of claim 1, further comprising adding a new solution to an existing problem on the machine readable medium.

11. A method for providing problem, and solution information to a plurality of medical diagnostic systems, the method comprising:
- storing in a distribution system a first problem and a second problem, the first and second problems having respective first and second solutions;
- establishing network links between the distribution system and first and second diagnostic systems;
- transmitting data descriptive of the first solution to the first diagnostic system and data descriptive of the second solution to the second diagnostic system; and
- displaying at the first and second diagnostic systems indicia descriptive of the respective first and second solutions.

12. The method of claim 11, wherein the first problem and first solution are adapted to the first diagnostic system, and the second problem and second solution are adapted to the second diagnostic system.

13. The method of claim 11, wherein at least one of the first and second diagnostic systems is a magnetic resonance imaging system.

14. The method of claim 11, wherein at least one of the first and second diagnostic systems is a computed tomography imaging system.

15. The method of claim 11, wherein at least one of the first and second diagnostic systems is an x-ray imaging system.

16. The method of claim 11, further comprising transmitting the first solution to the first diagnostic system.

17. The method of claim 11, further comprising:
- configuring a first problem query at the first diagnostic system and a second problem query at the second diagnostic system;
- transmitting the first and second queries to the distribution system; and
- transmitting the first and second solutions to the respective first and second diagnostic systems, the first and second solutions being displayed in response to the respective first and second queries.

18. The method of claim 11, further comprising adding a third problem to the distribution system, the third problem having an associated third solution.

19. The method of claim 11, further comprising adding to the distribution system an additional first solution corresponding to the first problem.

20. The method of claim 11, wherein the network links are initiated by the first and second diagnostic systems.

21. The method of claim 11, wherein the distribution system comprises a machine readable media.

22. The method of claim 11, further comprising verifying a subscriber status for the first diagnostic system prior to transmitting the first solution.

23. The method of claim 11, wherein the distribution system includes a first media for storing the first problem and first solution and a second media for storing the second problem and second solution.

24. The method of claim 23, wherein at least one of the first and second media comprise a portable machine readable data storage device.

25. A method for obtaining a solution to a problem with a medical diagnostic or management system, the method comprising:
- inputting a problem query on a user interface at the system;
- establishing a network link with a remote problem and solution library;
- accessing data from the library;
- viewing on the user interface a solutions list in response to the query;
- selecting a desired solution from the list; and
- transmitting the data from the library to the system.

26. The method of claim 25, wherein establishing the network link is performed prior to inputting the problem query.

27. The method of claim 25, wherein the data accessible by the system is a subset of the data in the library.

28. The method of claim 27, wherein the library includes problems and solutions for a plurality of diagnostic system modalities, and wherein the solutions list includes only solutions for a modality of a medical diagnostic system.

29. The method of claim 25, further comprising updating the library.

30. The method of claim 29, wherein updating the library includes adding a new problem and an associated solution to the library.

31. The method of claim 30, further comprising assigning an access tag to the new problem, the access tag identifying whether the problem is accessible by the system.

32. The method of claim 29, wherein updating the library includes adding a new solution to an existing problem.

* * * * *